United States Patent [19]

Yamashita et al.

[11] Patent Number: 4,903,203
[45] Date of Patent: Feb. 20, 1990

[54] BONE EVALUATION METHOD

[75] Inventors: Gentaro Yamashita, Tachikawa; Yasuhiro Uotani, Koshigaya; Yoshio Hirano, Setagaya, all of Japan

[73] Assignee: Teijin Limited, Osaka, Japan

[21] Appl. No.: 929,308

[22] Filed: Nov. 12, 1986

[30] Foreign Application Priority Data

Nov. 11, 1985 [JP] Japan .................. 60-250638
Feb. 7, 1986 [JP] Japan .................. 61-24151

[51] Int. Cl.$^4$ .................................. G06F 15/42
[52] U.S. Cl. .................... 364/413.15; 128/653 R; 378/54; 364/413.2
[58] Field of Search ............. 364/414, 413.15, 413.2; 128/653, 659; 378/54, 55, 56

[56] References Cited

U.S. PATENT DOCUMENTS

| | | | |
|---|---|---|---|
| 3,944,830 | 3/1976 | Dissing | 250/358 R |
| 4,442,404 | 4/1984 | Bergmann | 324/309 |
| 4,499,540 | 2/1985 | Kowalski | 364/414 |
| 4,593,355 | 6/1986 | Chase | 364/415 X |
| 4,618,975 | 10/1986 | Glantschnig | 364/414 X |
| 4,635,643 | 1/1987 | Brown | 324/308 X |
| 4,663,772 | 5/1987 | Mattson | 364/414 X |
| 4,721,112 | 1/1988 | Hirano | 128/653 |

FOREIGN PATENT DOCUMENTS 1316041 5/1973 United Kingdom .

OTHER PUBLICATIONS

Mayhan, Robert J.—Discrete-Time and Continuous-Time Linear Systems—Addison-Wesley Publishing Co., 1984, p. 399.

Inoue et al., "Quantitative Assessment of Bone Density on X-Ray Picture", Journal of the Japanese Orthopaedic Assn., vol. 57, No. 12, 1983, pp. 103–116.

"Measurement of Bone Mineral in vivo: An Improved Method", Science, vol. 142, (1963), pp. 230–231.

Primary Examiner—Jerry Smith
Assistant Examiner—Steven G. Kibby
Attorney, Agent, or Firm—Sughrue, Mion, Zinn, Macpeak & Seas

[57] ABSTRACT

A method for evaluating cancellous bone from a density pattern of the cancellous bone obtained by irradiating the cancellous bone with a radiation wherein trabeculae of the cancellous bone are analyzed based on a power spectrum obtained by a Fourier transformation of the density pattern is provided.

Furthermore, a method for evaluating cancellous bone from the density pattern of the cancellous bone obtained by irradiating the cancellous bone with radiation, wherein the density pattern is determined by irradiating the radiation substantially vertically against the main trabecula of the cancellous bone and the degree of the bone atrophy of the cancellous bone is evaluated by using the area ($\Sigma GS$) of the density pattern and/or the value ($\Sigma GS/D$) obtained by dividing the area ($\Sigma GS$) by the bone width (D) of the cancellous bone.

17 Claims, 4 Drawing Sheets

BONE EVALUATION METHOD

BACKGROUND OF THE INVENTION

1. Field of the Invention

The present invention relates to a bone evaluation method. More specifically, it relates to a bone evaluation method in which a cancellous bone is evaluated based on a bone density pattern (i.e. a graph obtained through scanning the bone or the X-ray film and plotting the intensity of transmitted photon beam or X-ray) of the cancellous bone. For the evaluation of bones, the bone density pattern is transformed to power spectrum through the algorithm of the Fourier transformation or is processed to calculate the parameters of bone atrophy such as the area ($\Sigma GS$) of the bone density pattern and/or the value ($\Sigma GS/D$) obtained by dividing the area ($\Sigma GS$) by the bone width (D).

2. Description of the Related Art

The human bones are generally subdivided into cortical bone and cancellous bone. The cortical bone is dense osseous tissue and is represented by the diaphysis of appendicular skelton in the form of pipes. On the other hand, cancellous bone consists mainly of trabeculae. Such cancellous bone is present, for example, in the epiphysial portions of long shaft bones, vertebrae, carpal bones, calcanei, tali, and tarsal bones. However, since cancellous bone has a larger surface in contact with soft tissue containing vasculatures, cancellous bone shows higher metabolic turn over and is predisposed to rapid changes under bone diseases or treatments.

The so-called MD method is known as a method for evaluating cortical bones, for example, growth conditions of human skelton, bone age, or kinds of bone diseases such as osteoporosis and osteomalacia, as disclosed in, for example, "Kotsu Taisha" (i.e., Bone Metabolism) 13, pp 187-195 (1980) and 14, pp 91-104, (1981). The improved MD method is disclosed in, for example, "Kotsu Keitai Keisoku" (i.e., "Bone Morphometry") 5, 36-46 (1983).

On the other hand, a method is known of evaluating the cancellous bone whereby the bone is evaluated by analysing changes in the trabeculae from a plane X-ray of the cancellous bone. That is, the distribution of trabeculae of the cancellous bone depends upon the stress distribution applied to the bones, and bones contain thick trabeculae supporting the body weight (i.e., principal trabeculae) as well as thin trabeculae linking the thick trabeculae (i.e., subtrabeculae). When the bone volume is decreased due to diseases such as osteoporosis, commonly the subtrabeculae are first absorbed and the principal trabeculae are retained in a relatively good condition. Accordingly, various methods for evaluating the degree of bone atrophy were developed utilizing the above-mentioned common occurrence. For example, the Itami's classification for the spine, the Singh's classification for the neck of the femur, and the so-called calcaneal index for calcanei are known (see Osteoporosis (Kiso and Rinsho), T. Fujita et al, pages 331-337; published on Nov., 1983 by Kyowakikaku Tsushin; J. Bone and Joint Surg., Vol. 65 B, No. 2, p 195-198 (1983); and J. Bone and Joint Surg., Vol. 52 A, 457 (1970)).

However, all these methods evaluate the degree of bone atrophy by the visual observation of plane X-ray photographs and, therefore, are unsatisfactory from an objective standpoint. Furthermore, the accuracy of these methods is insufficient to distinguish minor changes in the bone diseases, and thus, there is a strong need to develop a method for objectively and quantitatively evaluating the conditions of cancellous bone.

SUMMARY OF THE INVENTION

Accordingly, the objects of the present invention are to eliminate the above-mentioned disadvantages of the conventional bone evaluation methods and to provide a novel bone evaluation method capable of objective and quantitative evaluation of cancellous tissue in bones such as calcanei and vertebrae with a good reproducibility.

Other objects and advantages of the present invention will be apparent from the following description.

In accordance with the present invention, there is provided a method for evaluating cancellous bone by the steps of:

Obtaining a density pattern of the cancellous bone by measuring the intensity of transmitted radiation through the cancellous bone wherein trabeculae of the cancellous bone are analyzed based on a power spectrum obtained by a Fourier transformation of the density pattern.

In accordance with the present invention, there is also provided a method for evaluating cancellous bone from the density pattern of the cancellous bone obtained by irradiating the cancellous bone with radiation, wherein the density pattern is determined by irradiating the radiation substantially perpendicularly against the main trabecula of the cancellous bone and the degree of bone atropy of the cancellous bone is evaluated by using the area ($\Sigma GS$) of the density pattern and/or the value ($\Sigma GS/D$) obtained by dividing the area ($\Sigma GS$) by the width (D) of the cancellous bone.

BRIEF DESCRIPTION OF THE DRAWINGS

The present invention will be better understood from the description set forth below with reference to the accompanying drawings, wherein.

DESCRIPTION OF THE PREFERRED EMBODIMENTS

A first aspect of the present invention will now be explained.

According to the present invention, when a cancellous bone is evaluated, a bone density pattern is first determined by measuring the photodensity of an X-ray photograph of the cancellous bone or by scanning the cancellous bone with photon beam.

For the evaluation of the cancellous bone, calcanei, the spine, carpal bones, talus, tarsal bones, the epiphysial portions of long bones, and the like are most suitable. The X-ray photograph can be taken by any conventional X-ray photographic method and the desired bone density pattern can be obtained by measuring the photodensity of the resultant X-ray photograph. The bone pattern can be determined, for example, according to a conventional MD method. That is, the photodensity of the X-ray photograph is measured, together with the X-ray photograph of an aluminum step wedge consisting of, for example, 20 steps each having a minimum height of 1 mm and a maximum height of 20 mm), or an aluminum slope, by means of a densitometer.

Alternatively, the X-ray photograph of the bone is read, together with that of the aluminum step wedge or aluminum slope, by a video camera, to determine the bone density pattern.

When determining the bone density pattern, preferably the photo density of the bone taken by an X-ray photograph is read substantially perpendicularly against the main trabecula of the cancellous bone. This is because, when the X-ray photograph is read substantially perpendicularly against the main trabecula of the cancellous bone, a density pattern most preferably reflecting the principal trabeculae of the cancellous bone can be obtained.

Figure 1:
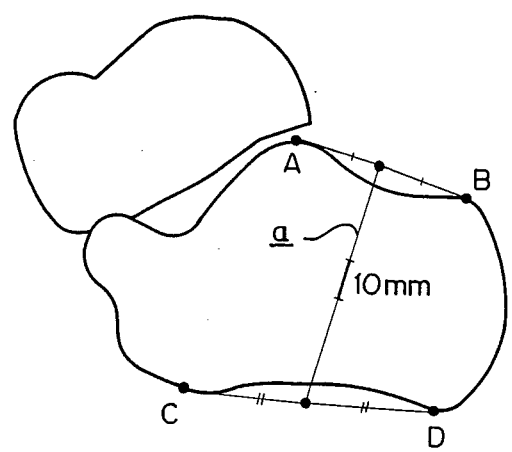
FIG. 1 illustrates an X-ray photographic image of a calcaneus.
Figure 2:
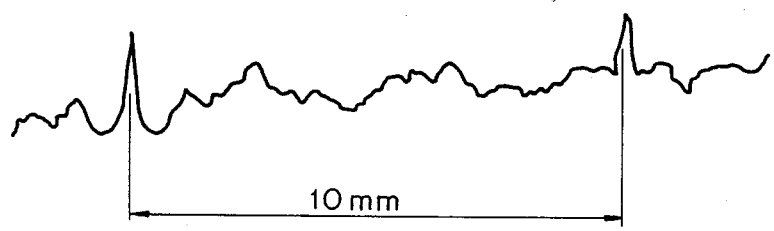
FIG. 2 illustrates a bone density pattern obtained from the X-ray photographic image shown in FIG. 1.

As an example, the bone evaluation method according to the present invention will now be explained in the case of a calcaneus. FIG. 1 schematically illustrates an X-ray photographic image of a calcaneus. The density pattern is determined, to obtain a wave spectrum most accurately reflecting the main trabecula of the calcaneus, as follows. That is, a line a is drawn, for example, between the center of the points A and B and the center of the points C and D and the photodensity, for example, at a 10 mm portion in the center portion of line a is read, and thus, a density pattern is obtained. The density pattern most preferably reflecting the main trabecula is as shown in FIG. 2. However, it should be noted that the line a can be drawn, for example, between the center of the points A and B and the point C of the bony prominence.

On the other hand, the bone density pattern can be obtained from the cancellous bone by photon absorptiometry. According to the photon absorptiometry method, a photon beam is used instead of an X-ray and the amount of the photon transmitted through the bone is quantitatively counted by a detector (see "Science" Vol. 142, pp 230 (1963)). In this method, the cross-section of the cancellous bone is scanned by a photon and the count numbers of the photon transmitted through the bone are plotted as an image as shown in FIG. 2.

The bone density pattern is then transformed, by a Fourier transformation, to obtain a power spectrum. Before processing with Fourier transformation, it is preferable to subtract the direct current component from the bone density pattern. More preferably, in order to eliminate the effects from heterogeneous aspect of the cross-sectional shape of the bone, the pattern is subtracted by a broad curve approximating the bone density pattern, which is obtained, for example, by processing the pattern with the least square method.

The Fourier transformation can be effected directly from the density pattern obtained above, but can also be effected after converting the maximum and the minimum values to 1.0 and 0, respectively, or after subtracting the direct current component from the pattern. In the Fourier transformation, the density pattern is developed, as a periodic function f(x), to a Fourier series:

$$f(x) = \frac{1}{2} a_0 + \sum_{n=1}^{\infty} (A_n \cos nx + B_n \sin nx)$$

Thus, the Fourier factors $A_n$, $\underline{B_n}$ # are determined. Then, a power spectrum $C_n$ is determined as follows:

$$C_n = \sqrt{A_n^2 + B_n^2}$$

These operations can be carried out by using the algorithm of fast Fourier transformation by a computer. The power spectrum thus obtained reflects the increase or decrease of the trabeculae of the cancellous bone.

Figure 3:
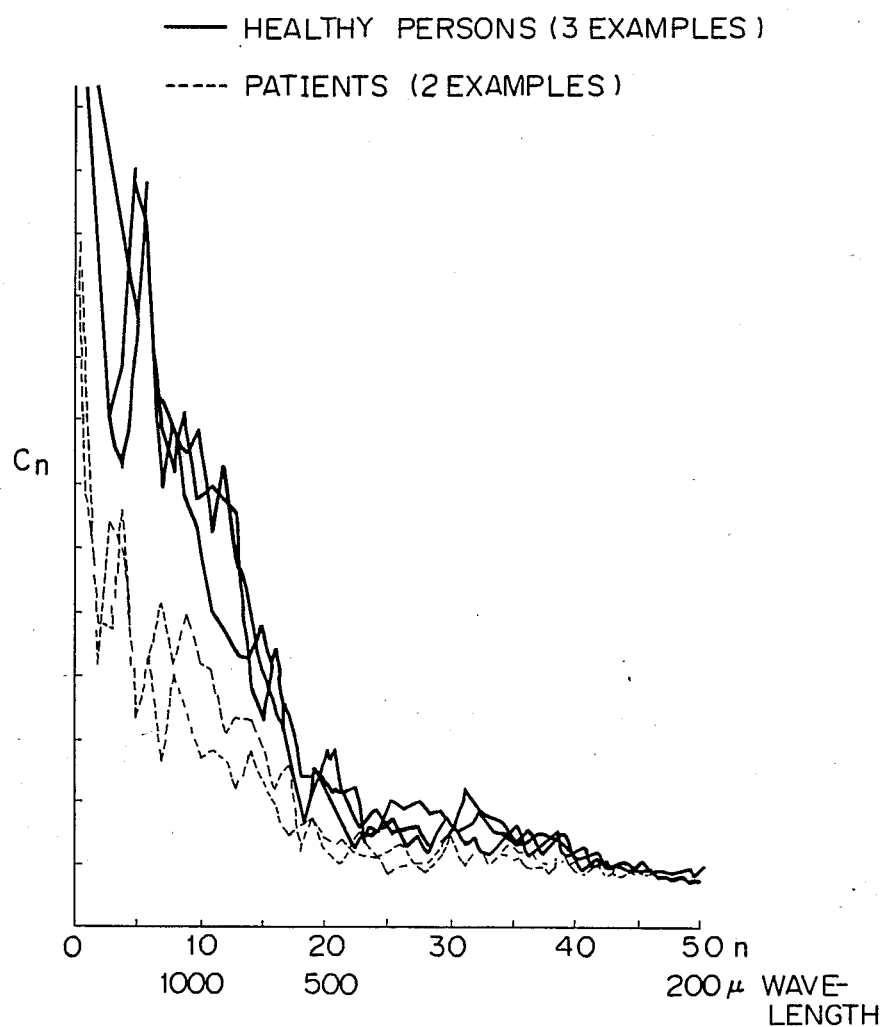
FIG. 3 illustrates a power spectrum obtained by a Fourier transformation of the bone density pattern.

A power spectrum as illustrated in FIG. 3 is obtained from FIG. 2 as follows. The density measurements of the 10 mm portions are made, for example, 10 times (preferably more than 10 times) by shifting the line a slightly in the parallel direction in FIG. 1, and are then subjected to the Fourier transformation. To obtain the density pattern of the 10 mm portion in FIG. 1, 256 samples of density data are read. Preferably, as large a number of data as possible is read for precise Fourier transformation. Thus, each $C_n$ value is obtained. After summing up these results, the curves shown in FIG. 3 can be obtained.

In FIG. 3, power spectra $C_n$ (i.e., solid line) obtained from the density patterns of calcanei of healthy persons and those $C_n$ (i.e., dotted line) obtained from the density patterns of senile osteoporosis patients are illustrated. As is clear from FIG. 3, the $C_n$ values of the healthy persons and those of the patients are remarkably different in the region nearby the point where n=10 (i.e., $C_{10}$). Accordingly, the trabeculae of cancellous bones can be analyzed by comparing the special $C_n$ values, e.g., $C_{10}$ values, after obtaining the $C_n$ values as mentioned above. Thus, the types of bone diseases, and the changes and progresses thereof, can be evaluated.

To make the evaluation from the power spectra more objective, the bone evaluation can be effected by comparing the ratio of the sum of the power spectra from n=5 to n=20 to that from n=40 to n=127. That is, in the case of senile osteoporosis, the ratio of the sum of the power spectra from n=5 to n=20 to that from n=40 to n=127 is remarkably small when compared to the ratio in the case of healthy persons.

Furthermore, the bone can be more objectively and quantitatively evaluated by combining the power spectrum obtained from the bone density pattern as mentioned above with the bone density distribution obtained from, for example, any conventional MD method.

As explained above, according to the present invention, a bone evaluation method capable of a more objective and more reliable evaluation of cancellous bones, especially calcanei, is provided.

A second aspect of the present invention will now be explained. As mentioned above, according to the second aspect of the present invention, the bone density pattern is first determined from X-ray photograph of the cancellous bone, especially the calcaneus, by measuring the photodensity of the X-ray photograph of the bone substantially perpendicularly against the main trabecula. Especially when calcanei are selected as the cancellous bones, the following advantages can be obtained.

1. The desired X-ray photograph can be easily obtained with a good reproducibility by imaging the calcaneus-portion on an X-ray film.

2. The amounts of soft tissues are relatively small and, therefore, adverse effects from soft tissues are optimally negligible.

3. The photodensity pattern of the bone can be determined with a good reproducibility since the portion to be measured can be relatively easily specified.

The X-ray image of, for example, calcaneus, can be obtained by taking the X-ray photograph, together with an aluminum step wedge or aluminum slope as mentioned above, by imaging the calcaneus on an X-ray film. The density pattern of the bone can be obtained by determining the X-ray image photodensity substantially perpendicularly against the main trabecula. This is because, when the density is read substantially perpendicularly against the main trabecula, the bone density pattern most preferably reflecting the calcaneus can be obtained. The bone density pattern can be determined in the same manner as explained in the first aspect of the present invention.

Figure 4:
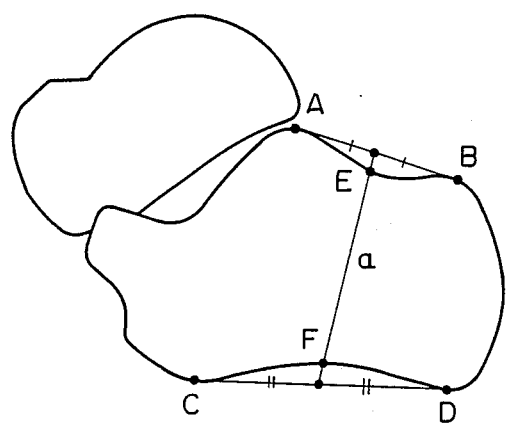
FIGS. 4 and 5 illustrate X-ray photographic images of a calcaneus.
Figure 5:
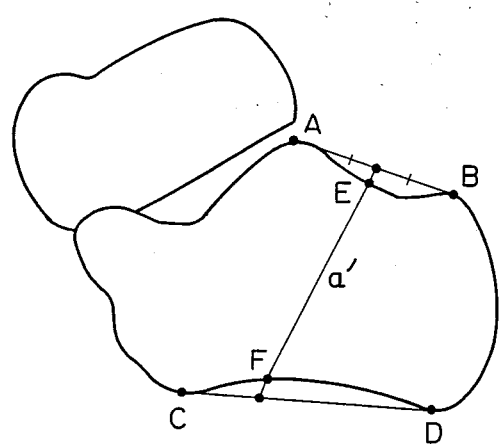

FIG. 4 schematically illustrates the X-ray pattern of the calcaneus. As mentioned above, to obtain the desired bone density pattern most preferably reflecting the main trabecula of, for example, a calcaneus, a straight line a is drawn, for example, between the center of the points A and B of the X-ray image and the center of the points C and D, as illustrated in FIG. 4. Thus, the photodensity of the X-ray image of the bone can be determined along the straight line a. However, as illustrated in FIG. 5, it is more preferable to determine the photodensity along the line a', which is drawn between the center of the points A and B and the point one-third the length of the line CD from the point C. Thus, the desired photodensity of the X-ray image of the bone can be determined more perpendicularly against the main trabecula.

Figure 6:
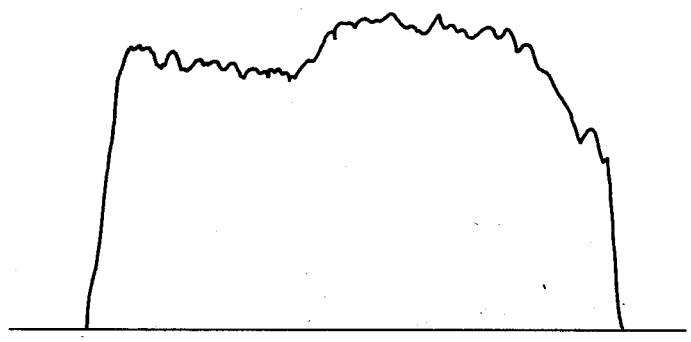
FIG. 6 illustrate a bone density pattern obtained from the X-ray photographic image shown in FIGS. 4 and 5.

The bone density pattern as illustrated in FIG. 6 can be obtained as mentioned above. The resultant bone density pattern is the photograph calibrated and converted to the bone density in relation to the aluminum thickness and the corresponding photodensity in terms of aluminum thickness (GS, i.e., gray scale). From the bone density pattern, the area index ($\Sigma$GS) is first obtained by integrating the value (GS), which is obtained by converting the bone density to the corresponding aluminum thickness, and the area ($\Sigma$GS) is then divided by the bone width (D) to obtain the index $\Sigma$GS/D. The bone width (D) can be obtained by measuring the distance EF in FIG. 4 with a measuring scale or a slide gage. The conditions of the calcaneus can be evaluated by using these indices. That is, the larger index ($\Sigma$GS) signifies a larger bone density of the calcaneus, whereas the smaller index ($\Sigma$GS) signifies a decrease in the bone density of the calcaneus. Thus, the area ($\Sigma$GS) can be advantageously used as an index for evaluating the degree of bone atrophy of the calcaneus.

Furthermore, the index ($\Sigma$GS/D) represents an average bone density and, therefore, can be preferably used as an index for evaluating the degree of bone atrophy without being affected by the bone width of the calcaneus. That is, when the index $\Sigma$GS is used for the evaluation, the value $\Sigma$GS becomes large when the bone width D is large. Contrary to this, the value $\Sigma$GS/D is not affected by the bone width and, therefore, a more objective and quantitative determination of the bone density can be effected when the value $\Sigma$GS/D is used. Thus, the use of the value $\Sigma$GS/D is preferable as an index for representing the degree of bone atrophy of the calcaneus. It should be noted that the evaluation can be carried out by using both of the indices $\Sigma$GS and $\Sigma$GS/D.

As explained above, according to the present invention, a more objective and more quantitative evaluation of cancellous bones, especially trabeculae, can be carried out with a good reproducibility.

EXAMPLES

The present invention will now be further illustrated by, but is by no means limited to, the following Examples.

Example 1

An X-ray image was obtained by taking an X-ray photograph of the calcaneus of a woman aged 55 with osteoporosis. From this X-ray image, the auxiliary line a was drawn as illustrated in FIG. 1. The bone density pattern illustrated in FIG. 2 was obtained by reading the photodensity of the central 10 mm portion of the auxiliary line a with a densitometer and 256 samples were recorded. Similar operations were repeated 10 times by slightly shifting the auxiliary line a in a parallel direction to obtain the density patterns.

The above-mentioned density patterns were subjected to Fourier transformation to obtain the $C_n$ values. The $C_n$ values were summed and the results of the Fourier transformation were plotted as shown in FIG. 3.

In the same manner as mentioned above, the $C_n$ values were obtained from the calcanei of healthy persons. The results are shown in FIG. 3.

As clear from FIG. 3, the power spectrum values of the patients with senile osteoporosis are lower than those of the healthy person in the region nearby $n=10$. Furthermore, the ratios of the sum of the power spectra from $n=5$ up to $n=20$ to that of from $n=40$ to $n=127$ were about 0.07 in the case of the patients with senile osteoporosis and about 0.12 in the case of the healthy persons. Thus, it is clear that the cancellous bone can be evaluated by the power spectra obtained from the wave spectra of the Fourier transformation.

Example 2

Three X-ray photographic images were obtained by taking X-ray photographs of a calcaneus of a healthy man aged 35 under the same conditions, together with an aluminum step wedge consisting of 20 steps, each step having a height of 1 mm.

In one X-ray image of those obtained above, the photodensity patterns were measured three times along line a' of FIG. 5 with a microdensitometer. The results were enlarged twice and were then plotted in a chart. The densitometry of the X-ray imaging of the aluminum step wedge was determined at the same time. For determining one of the three calcaneus densitometry, the value $\Sigma$GS was calculated by integrating the area of the photodensity pattern of the bone which was to be converted in terms of aluminum thickness (GS) three times by using a computer. The other X-ray images were each subjected to one measurement with microdensitometer, and each microdensimetry was integrated once with a computer. The bone width D was measured with a slide gage.

From the determination results obtained above, the calculation error of the computer, the determination error of the densitometer, and the photographic error of the X-ray image were determined as a valuation factor CV:

$$CV = \frac{\sigma}{\overline{X}} \times 100 \, (\%)$$

The results are shown in Table 1. From the results shown in Table 1, it is clear that the errors are all very small.

TABLE 1

| Error | Index | | |
|---|---|---|---|
| | D | ΣCS | ΣGS/D |
| Computer analyzing | 0.32 | 0.51 | 0.51 |
| Densitometer measurement | 0.06 | 0.69 | 0.77 |
| X-ray image formation | 0.66 | 1.87 | 1.78 |

Thus, the evaluation error using the X-ray image of the calcaneus is very small and the evaluation results exhibit a good reproducibility.

Example 3

The bone densities of the calcanei of healthy persons, hemodialysis patients, and osteoporosis patients were determined in the same manner as in Example 2.

The results are shown in Table 2.

TABLE 2

| No. | Age | Sex | Disease | D | ΣGS | ΣGS/D |
|---|---|---|---|---|---|---|
| 1 | 21 | Female | Healthy | 7.84 | 17.88 | 2.28 |
| 2 | 28 | Male | Healthy | 8.53 | 17.53 | 2.06 |
| 3 | 36 | Male | Healthy | 10.35 | 22.89 | 2.21 |
| 4 | 27 | Male | Dialysis 2.3 year | 9.23 | 14.95 | 1.62 |
| 5 | 28 | Male | Dialysis 1.6 year | 10.05 | 19.57 | 1.95 |
| 6 | 59 | Female | Dialysis 10 year | 8.77 | 14.88 | 1.70 |
| 7 | 72 | Female | Osteroporosis | 9.21 | 8.39 | 0.91 |
| 8 | 79 | Female | Osteroporosis | 9.34 | 13.05 | 1.40 |
| 9 | 82 | Female | Osteroporosis | 8.86 | 12.98 | 1.46 |
| 10 | 82 | Female | Osteroporosis | 8.83 | 14.30 | 1.62 |

As is clear from the results shown in Table 2, the ΣGS and ΣGS/D of the hemodialysis patients and osteoporosis patients with a progressive or advanced degree of bone atrophy are small when compared to those of the healthy persons. Thus, the ΣGS and ΣGS/D obtained from the X-ray photographic images of the calcanei can be effectively and advantageously used as indices for bone evaluation.

What is claimed:

1. A method for evaluating cancellous bone comprising the steps of:
   (a) irradiating cancellous bone with radiation;
   (b) measuring the transmitted radiation to form a bone density pattern;
   (c) directly transforming the density pattern by a Fourier transformation as a periodic function of f(x) to a Fourier series:

$$f(x) = \tfrac{1}{2}a_0 + \sum_{n=1}^{\infty} (An \cos nx + Bn \sin nx)$$

to determine the Fourier factors An and Bn followed by determining a power spectrum Cn as follows:

$$Cn = \sqrt{An^2 + Bn^2}$$

and plotting the power spectrum $C_n$.

2. A method according to claim 1, wherein the radiation is a photon beam and the beam density pattern is formed by direct monitoring.

3. A method according to claim 1, wherein the radiation is X-ray and the density pattern is based on densitometric measurement of an X-ray photograph of the cancellous bone.

4. A method as in claim 1, wherein the radiation is passed perpendicularly through the main trabeculae of the cancellous bone.

5. A method according to claim 1, further comprising subtracting a direct current component from the density pattern prior to Fourier transformation.

6. A method according to claim 5, wherein the direct current component stands for a straight line approximating the bone density pattern.

7. A method according to claim 5, wherein the direct current component stands for a broad curve approximating the bone density pattern.

8. A method according to claim 1, wherein the cancellous bone is at least one member selected from the group consisting of a calcaneus, spine, carpal bone, tarsal bone, talus, and an epiphsial portion of long bone.

9. A method according to claim 1 wherein density measurements are made over at least 10 different 10 millimeter segments of cancellous bone, and the Power Spectra value is averaged.

10. A method for evaluating cancellous bone according to claim 1 further comprising obtaining the first and second sums of the power spectra at a first and second regions of the power spectra and comparing the first and second sums to obtain a ratio thereof.

11. A method for evaluating cancellous bone as claimed in claim 10, wherein the first and second regions are a region of from n=5 to n=20 of the power spectra and a region of from n=40 to n=127 of the power spectra, respectively.

12. A method for evaluating a calcaneus comprising the steps of:
   (a) irradiating the calcaneus substantially perpendicularly against the principle trabeculae of the calcaneus with radiation to obtain a density pattern;
   (b) calculating the area (ΣGS) of the density pattern;
   (c) evaluating the degree of the bone atrophy by using the area (ΣGS);
   (d) transforming the density pattern by Fourier transformation to obtain a power spectrum; and
   (e) evaluating the trabeculae of the calcaneus based on the power spectrum.

13. A method according to claim 12 wherein the Fourier transformation is effected directly from the density pattern as a periodic function of f(x) to a Fourier series:

$$f(x) = \tfrac{1}{2}a_0 + \sum_{n=1}^{\infty} (An \cos nx + Bn \sin nx)$$

to determine the Fourier factors An and Bn, followed by determining a power spectrum Cn as follows:

$$Cn = \sqrt{An^2 + Bn^2}$$

and further comprising plotting the power spectrum $C_n$.

14. A method for evaluating a calcaneus comprising the steps of:

(a) irradiating the calcaneus substantially perpendicularly against the principle trabeculae of the calcaneus with radiation to obtain a density pattern;
(b) measuring the bone width (D);
(c) calculating the area (ΣGS) of the density pattern corresponding to the bone width (D);
(d) evaluating the degree of the bone atrophy by using the value (ΣGS/D) obtained by dividing the area (ΣGS) by the bone width (D) of the calcaneus;
(e) transforming the density pattern by Fourier transformation to obtain a power spectrum; and
(f) evaluating the trabeculae of the calcaneus based on the power spectrum.

15. A method according to claim 14, wherein the Fourier transformation is effected directly from the density pattern as a periodic function of f(x) to a Fourier series:

$$f(x) = \frac{1}{2} a_0 + \sum_{n=1}^{\infty} (A_n \cos nx + B_n \sin nx)$$

to determine the Fourier factors An and Bn, followed by determining a power spectrum Cn as follows:

$$Cn = \sqrt{A_n^2 + B_n^2}$$

and further comprising plotting the power spectrum $C_n$.

16. A method for evaluating a calcaneus comprising the steps of:

(a) irradiating the calcaneus substantially perpendicularly against the principle trabeculae of the calcaneus with radiation to obtain a density pattern;
(b) measuring the bone width (D);
(c) calculating the area (ΣGS) of the density pattern corresponding to the bone width (D);
(d) evaluating the degree of the bone atrophy by using the area (ΣGS/D) and the value (ΣGS/D) obtained by dividing the area (ΣGS) by the bone width (D) of the calcaneus;
(e) transforming the density pattern by Fourier transformation to obtain a power spectrum, and
(f) evaluating the trabeculae of the calcaneus based on the power spectrum.

17. A method according to claim 16 wherein the Fourier transformation is effected directly from the density pattern as a periodic function of f(x) to a Fourier series:

$$f(x) = \frac{1}{2} a_0 + \sum_{n=1}^{\infty} (A_n \cos nx + B_n \sin nx)$$

to determine the Fourier factors An and Bn, followed by determining a power spectrum Cn as follows:

$$Cn = \sqrt{A_n^2 + B_n^2}$$

and further comprising plotting the power spectrum $C_n$.

* * * * *